United States Patent [19]

Schneider et al.

[11] Patent Number: 4,641,534
[45] Date of Patent: Feb. 10, 1987

[54] HOLDING DEVICE

[75] Inventors: Ortwin Schneider, Weiterstadt; Nikolaos Georgitsis, Heusenstamm, both of Fed. Rep. of Germany

[73] Assignee: Erweka Apparatebau GmbH, Heusenstamm, Fed. Rep. of Germany

[21] Appl. No.: 782,503

[22] Filed: Oct. 1, 1985

[30] Foreign Application Priority Data

Jun. 3, 1985 [DE] Fed. Rep. of Germany ... 8516163[U]

[51] Int. Cl.⁴ ............................................. G01N 3/02
[52] U.S. Cl. ........................................ 73/856; 73/821
[58] Field of Search ................. 73/819, 821, 823, 824, 73/818, 822, 825, 856, 859, 860

[56] References Cited

U.S. PATENT DOCUMENTS

| | | | |
|---|---|---|---|
| 3,368,674 | 2/1968 | Koeppe | 73/819 |
| 4,092,843 | 6/1978 | Matskevich et al. | 73/822 |
| 4,542,646 | 9/1985 | Smith et al. | 73/821 |

FOREIGN PATENT DOCUMENTS 2812257 10/1979 Fed. Rep. of Germany ........ 73/821

Primary Examiner—Stewart J. Levy
Assistant Examiner—Robert R. Raevis
Attorney, Agent, or Firm—Birch, Stewart, Kolasch & Birch

[57] ABSTRACT

A holding device for holding test samples, in particular tablets, in a testing station for measuring the breaking strength of the test samples comprises a supporting structure carrying a rotatable mounting support supporting a plurality of press pads having gripper means or a cushion at their lower ends for being adapted to the shapes of the samples, each press pad being adapted to one particular sample shape, and which press pads align and/or hold the samples on a base plate. A drive means is provided for rotating the mounting support such that the press pad suitable for a particular sample is brought into an operating position in the testing station. A lowering means is operative for lowering the respective press pad just being in the operating position down to the base plate in order to align and/or hold the sample in the testing station.

16 Claims, 4 Drawing Figures

HOLDING DEVICE

BACKGROUND OF THE INVENTION

The invention relates to a holding device for test samples, in particular tablets and the like.

A testing device for examining test samples in the form of tablets in respect of weight, thickness and breaking strength is known from West German Utility Model No. 84 02 581. In this device the samples are intermittently conveyed by means of a conveying device to a balance, to a thickness gauge and to a gauge for carrying out the breaking strength test. In the breaking strength test, the tablet rests on a base plate, engages an abutment on one side and is pressed by a post against the abutment from the side opposite to the abutment. The force which is exerted by the post to the tablet and which is just enough to break the tablet is the characteristic mechanical value of the tablet which is to be measured. There are no problems when measuring the breaking strength of tablets having lenticular or spherical shapes since the tablets take—because of their particular symetrical shape—automatically the correct position between the abutment and the post as long as they are held down on the base plate. However, when the tablet samples are rod-shaped, elongated, oval or heart-shaped, there is the problem to correctly align the samples between the abutment and the post. The correct alignment is defined such that the longitudinal axis of a rod-shaped sample or the longer diameter axis of an elongated or oval sample is orientated in the direction in which the post exerts a force on the sample. In the case of heart-shaped samples, the force must be applied in the direction from the bottom (peak) of the heart to the top. If the samples are not orientated in the desired direction during the breaking strength test, the measurements are incorrect.

GENERAL OUTLINE OF THE INVENTION

It is, therefore, the object of the invention to provide a holding device which is capable of exactly aligning and/or holding the test samples, in particular tablets, in a breaking strength test station also in such cases where the samples are rod-shaped, elongated oval or heart-shaped.

To carry-out this object, a holding device for holding test samples, in particular tablets, in a testing station for measuring the breaking strength of the testing samples comprises a supporting structure carrying a movable mounting support supporting a plurality of press pads which are adapted to the shapes of the test samples, each press pad being adapted to one particular sample shape, and which press pads are adapted to align and/or hold said test samples on a base plate, a drive means for moving said mounting support in such a manner that the press pad suitable for the respective sample is brought into an operating position in the testing station, and lowering means for lowering the respective press pad just being in the operating position down to the base plate in order to align and/or hold said sample in said testing position.

The holding device according to the invention has the advantage that, without requiring long setting periods, it provides the selection of a press pad which is suitable and adapted to the shape of the respective sample. The selection of the desired press pad may be performed automatically by a control unit, such as a computer, as a function of the shape of the samples to be examined.

The holding device has a particularly simple structure when the mounting support is rotatably supported by the supporting structure and the press pads are circularly disposed on the mounting support.

A preferred embodiment of the drive arrangement comprises an electric motor, which is disposed on the mounting support and which is connected with the supporting structure by means of a gearing, preferably a bevel gearing, so that the motor moves jointly with the mounting support.

In a preferred embodiment of the invention a simple structure of the lowering mechanism is achieved by an electric motor disposed on the supporting structure, the shaft of said electric motor having an eccentric. On rotation of the electric motor the eccentric lowers the press pad by means of a wheel disposed on said press pad against the force of a return spring. On further rotation of the eccentric the press pad is lifted by means of the return spring pressing the wheel against the eccentric.

At their lower ends the press pads have grippers suitable for the respective case of application, which grip and align the sample, or a cushion of elastic material, pressing the sample against the base plate. The cushion is used for lenticular or spherical samples whereas the grippers are used for samples having a non-circular shape as viewed from the top.

For exactly positioning the press pads in their respective operating positions it is advantageous to provide positioning devices. For stopping the mounting support in a zero position it is also convenient to provide a stop magnet which, in a preferred embodiment, is arranged at the supporting structure and the anchor of which magnet engages with a recess of the mounting support only if the mounting support is in the zero position.

LIST OF DIFFERENT VIEWS OF THE FIGURES

DETAILED ACCOUNT OF THE WORKING EXAMPLE OF THE INVENTION

Figure 1:
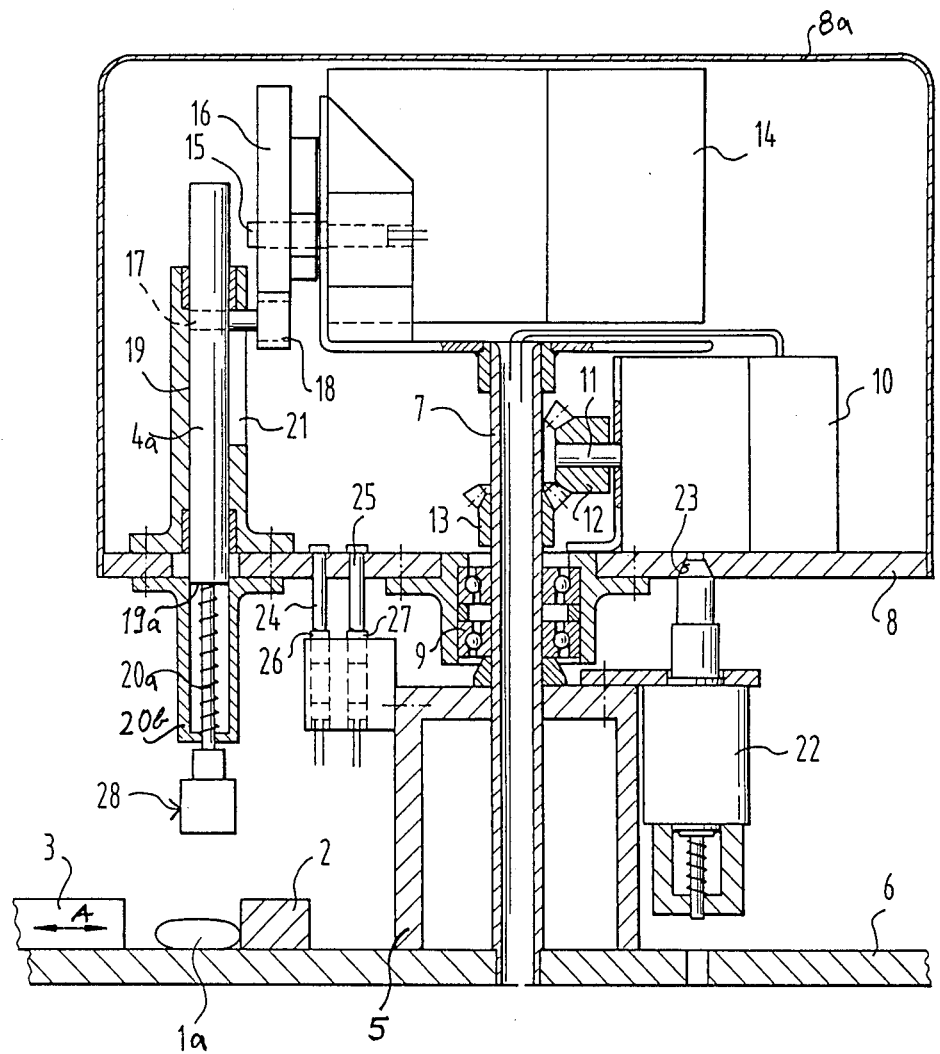
FIG. 1 is a sectional view of the holding device.
Figure 3:
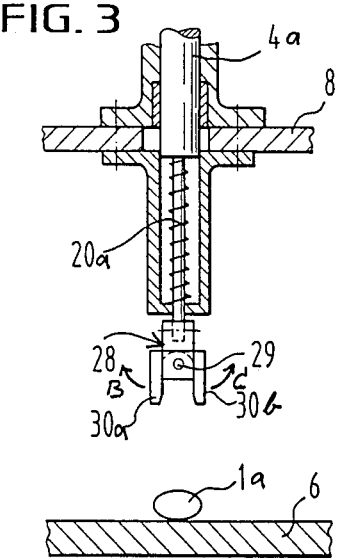
FIG. 3 shows a press pad provided with a gripper.

In FIG. 1, the holding device is shown in a position next to a testing station for measuring the breaking strength of samples 1a which take the form of tablets having a longitudinal shape, the long axis of sample 1a being shown in FIG. 1, and the small diameter—at 90 degrees to the long diameter—being shown in FIG. 3. The testing station comprises a base plate 6, an abutment 2 and a post 3 movable in direction of arrow A (FIG. 1) by a motor (not shown) and being connected to a force measuring device (not shown) which is adapted to measure the force exerted by post 3 onto sample 1a. The desired measurement is the force necessary to break the sample 1a in the direction of the long axis thereof as shown in FIG. 1. In order to make this measurement, the samples are conveyed by means of a conveying device, e.g. as shown in West German Utility Model No. 8402581, to a position in between the abutment 2 and the post 3. Subsequently, a suitable press pad 4a is lowered down on sample 1a in order to align it with its long axis in the direction of arrow A and hold it down in this position. Thereupon, a force in direction of arrow A is applied by post 3 to sample 1a sufficient to break the sample 1a, and this force is measured just prior to breakage of sample 1a. The testing station as such is the same for all different shapes of samples, e.g. disc-shaped, lenticular, spherical, rod-shaped, londitudinal, oval or heart-shaped samples. Also different sizes of such different types of samples are processed by one and the same testing station. Therefore, it is required to have suitable press pads for samples of different shapes and sizes as will be explained later.

The holding device comprises a supporting structure consisting of a stand 5 fixed to the base plate 6 and a column 7 anchored at its lower end in base plate 6 and being supported by the stand 5 at a position spaced above base plate 6. The stand 5 and the column 7 are stationary to the base plate 6. The holding device further comprises a movable mounting support 8 supporting the press pads 4a, 4b . . . The mounting support 8 is rotatably mounted by means of a bearing 9, the stationary part of which bearing is fixed to the column 7 and the stand 5 whereas the movable part of the bearing 9 is fixed to the mounting support 8. The mounting support 8 is rotated by an electric motor 10 which is fixed to the mounting support 8. The driving connection between the motor 10 and the stationary column 7 is made by a gearing comprising the bevel gears 12 and 13. Thus, a rotation of shaft 11 of the electric motor 10 results in a rotation of mounting support 8 together with the electric motor 10 around column 7.

The press pads 4a, 4b . . . are arranged on the mounting support 8 on a circle about the column 7, i.e. at equal distance from column 7. By turning the mounting support 8 about the column 7, a particular one of the press pads may, therefore, be brought into the operating position above a particular sample in the testing station.

The press pads 4a, 4b . . . are rod-shaped and supported to be moved vertically on the mounting support 8. For actuating the press pads to perform a downward movement, a lowering device comprising an electric motor 14 arranged on top of the column 7, and an eccentric actuating means is provided. The eccentric actuating means comprises an eccentric 16 arranged on shaft 15 of the electric motor 14, and a wheel 18 on an axle 17 connected to the rod-shaped body of the press pad 4a (FIG. 1). When the electric motor 10 has brought a suitable press pad, e.g. press pad 4a, to its operating position in the testing station, the wheel 18 of this press pad 4a is in a position to be operated by the eccentric 16. The wheel 18 is pressed against eccentric 16 by a return spring 20a which is seated between a shoulder 19a between a larger diameter portion and a smaller diameter portion of the rod-shaped body of the press pad 4a and a cup-shaped housing 20b surrounding the smaller diameter portion of the rod-shaped body and being fixed to the bottom side of mounting support 8. The return spring 20a, therefore, acts to force the press pad upwards and holds the press pad in an idle position. The rod-shaped body of the press pad 4a is guided in its vertical movement by the housing 20b and a guide tube 19 mounted on the top side of mounting support 8. On rotation of eccertric 16 by the electric motor 14, the press pad 4a is, therefore, lowered against the force of the return spring 20 until the press pad seizes the sample. As soon as eccentric 16 is further rotated, the press pad 4a is again lifted back to its idle position by the return spring 20a. For accomodating the axle 17, the guide tube 19 has a slot 21, the length of which corresponds to the length of the vertical movement of the press pad 4a. The holding device is designed to be operated by a control unit, e.g. a computer. In order to perform all functions of the holding device automatically by means of a control unit, it is preferred to have an adjusting means for adjusting the zero position of the mounting support. To this purpose there is provided a stop magnet 22 on the stand 5, the anchor of which stop magnet is adapted to engage a recess 23 in the mounting support 8. The zero position is given if the recess 23 is engaged by the anchor of the magnet 22. As soon as this zero position is verified, the anchor of the stop magnet 22 is removed from recess 23. Also in connection with the automatic control of the holding device, it is preferred to have sensing means for exactly verifying the positioning of the press pads in their operating position. This positioning device comprises a contact pin 24 on the mounting support 8 and an associated contact switch 26 mounted on the stand 5 opposite and close to the pin 24. The contact pin 24 actuates the contact switch 26, e.g. a read switch, if the mounting support 8 is in its zero position. The positioning device furthermore comprises a plurality of contact pins 25 on the mounting support 8 on equal distance from column 7, equal in number to the number of press pads and cooperating with an associated contact switch 27, e.g. a read switch, mounted on the stand 5 opposite and close to the pins 25. The actuation of the contact switch 27 by the contact pins 25 verifies the positions of the press pads in the operating position.

The magnet 22 is a mechanical means to verify the zero position that is in addition to the contact pin 24 and contact switch 26. When the anchor of the magnet 22 engages the recess 23, the mounting support 8 is exactly in its zero position, and this facilitates the adjustment of the electrical circuit of the read switch 26 to switch exactly in the zero position. The magnet 22 is, therefore, an additional means facilitating the adjustment of the whole apparatus.

Figure 2:
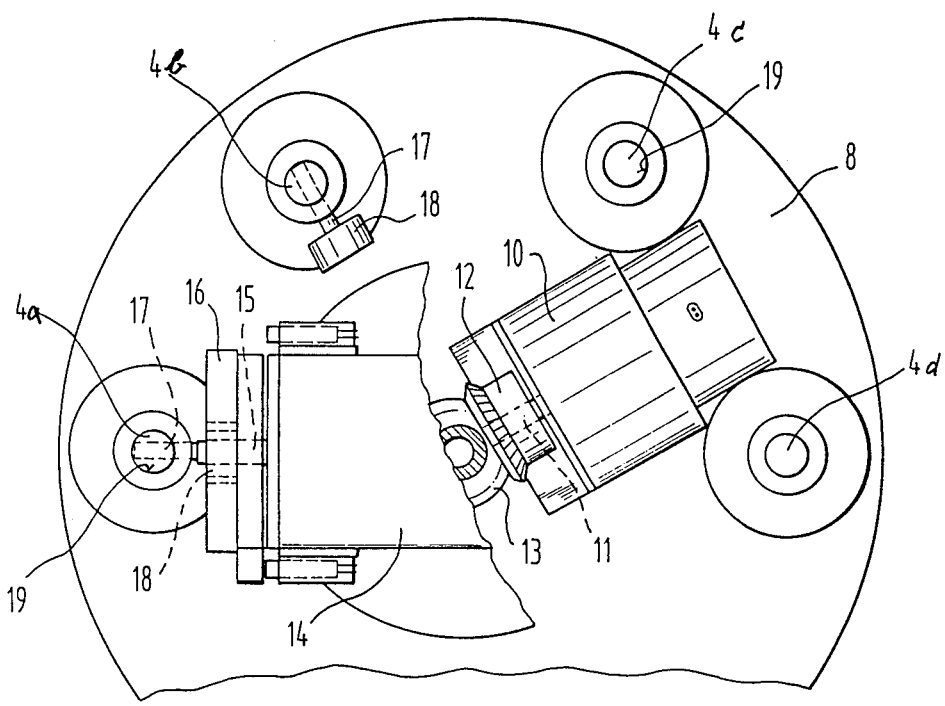
FIG. 2 is a plan view of press pads disposed in a mounting support.

FIG. 2 shows a plan view of the mounting support 8 without its cover 8a. In FIG. 2, the press pad 4a is in the operating position where it may be actuated by eccentric 16. Since part of the motor 14 is broken away, FIG. 2 also shows the electric motor 10 which is in an operative connection with column 7 by means of the bevel gears 12 and 13. It is understood that each of the press pads 4a, 4b, 4c and 4d has a wheel 18, although FIG. 2 shows such a wheel only with the two press pads 4a and 4b. It is, furthermore, to be understood that there are six press pads provided in this operating example of the invention, although there are shown only four of such press pads.

Figure 4:
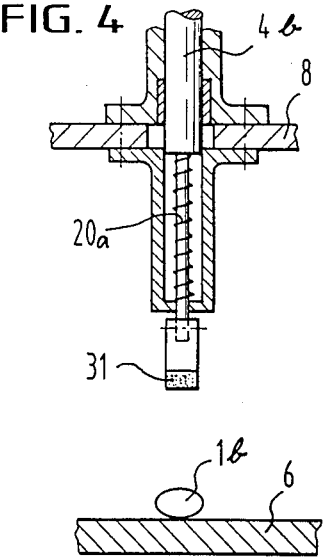
FIG. 4 shows a press pad provided with a cushion.

FIG. 3 shows a sideview of one type of a press pad 4a which has, at its lower end, gripper means 28 consisting of two angular jaws 30a, 30b which are at their upper angle portions swingably attached to an axis 29. This allows the jaws 30a, 30b to move in direction of the arrows B and C outwards when the jaws come into contact with sample 1a. Since the jaws 30a, 30b have some breadth in the direction perpendicular to FIG. 3 as can be seen also from FIG. 1, they align the sample 1a due to the gravity action of the jaws 30a, 30b when they are moved apart by the sample 1a. Due to the same gravity action, the jaws 30a, 30b also hold the sample 1a in the correct position between the abutment 2 and the post 3. Additionally, a spring (not shown) may be disposed between the jaws 30a, 30b so that the sample 1a can be seized more tightly. It is to be understood that the spacing between the jaws 30a, 30b and the breadth of the jaws in the direction perpendicular to FIG. 3 is selected according to the particular type of sample. In the preferred embodiment of the invention shown in the drawings, where six different kinds of press pads are used, five press pads may have five different gripper arrangements which are designed for five different types of samples. The remaining press pad which is shown as press pad 4b in FIG. 4 then contains at its lower end a cushion 31 of elastic material for holding lenticular or spherical or flat cylindrical samples.

It will be apparent that the preferred embodiment of the invention disclosed is well calculated to fulfill the object stated above, it will be appreciated that the invention is susceptible to modification, variation and change without departing from the proper scope of fair meaning of the subjoined claims.

We claim:

1. A holding device for holding test samples, in particular tablets, in a testing station for measuring the breaking strength of the test samples comprising
   a supporting structure carrying a movable mounting support supporting a plurality of press pads which are adapted to the shapes of the test samples, each press pad being adapted to one particular sample shape, and which press pads are adapted to hold said test samples on a base plate,
   a drive means for moving said mounting support in such a manner that the press pad suitable for the respective sample is brought into an operating position in the testing station, and
   lowering means for lowering the respective press pad just being in the operating position down to the base plate in order to hold said sample in said testing station.

2. A holding device according to claim 1, wherein the mounting support is rotatably supported on the supporting structure and the press pads are circularly arranged on the mounting support.

3. A holding device according to claim 2, wherein a return spring is provided for each of the press pads for lifting and holding said press pads in their idle positions.

4. A holding device according to claim 1, wherein the drive means comprises an electric motor mounted on the mounting support which electric motor is connected to the supporting structure by means of a gearing.

5. A holding device according to claim 4, wherein a return spring is provided for each of the press pads for lifting and holding said press pads in their idle positions.

6. A holding device according to claim 3, wherein the gearing is a bevel gearing containing a bevel gear arranged at the shaft of the electric motor and a bevel gear arranged at the column of the support structure.

7. A holding device according to claim 6, wherein a return spring is provided for each of the press pads for lifting and holding said press pads in their idle positions.

8. A holding device according to claim 1, wherein said lowering means comprises an electric motor arranged on the supporting structure, an eccentric arranged on the shaft of said electric motor, and a wheel adjacent to said eccentric and arranged on the press pad.

9. A holding device according to claim 8, wherein a return spring is provided for each of the press pads for lifting and holding said press pads in their idle positions.

10. A holding device according to any of claim 1, wherein a return spring is provided for each of the press pads for lifting and holding said press pads in their idle positions.

11. A holding device according to claim 1, wherein at least one of the press pads has, at its lower end, a cushion pressing said sample against the base plate to hold said sample in said testing station.

12. A holding device according to claim 1, wherein positioning devices are disposed at the mounting support and at the supporting structure respectively.

13. A holding device according to claim 1, wherein a stop magnet is provided at the supporting structure, the anchor of which stop magnet is adopted to engage a recess in the mounting support.

14. A holding deice according to claim 1, wherein at least one of the press pads has, at its lower end, means to hold and align said sample in said testing station.

15. A holding device according to claim 14, wherein said means to hold and align comprise gripper means partially embracing said sample.

16. A holding device according to claim 15, wherein said gripper means comprises two jaws which are, at their upper portions, swingably attached to a rotation axis.

* * * * *